United States Patent [19]

Stirnadel

[11] Patent Number: Plant 6,462

[45] Date of Patent: Dec. 13, 1988

[54] EUPHORBIA PLANT CV. STILOGA

[75] Inventor: Alfred Stirnadel, Zweibruchen-Oberauerbach, Fed. Rep. of Germany

[73] Assignee: Marianne Stirnadel-Schwab, Zweibrucken-Oberauerbach, Fed. Rep. of Germany

[21] Appl. No.: 80

[22] Filed: Jan. 2, 1987

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—William H. Elliott, Jr.; William T. King

[57] ABSTRACT

A new variety of Euphorbia cv. Stiloga characterized by its early production on strong solid stalks of from about 10 to 15 blossom clusters, each cluster consisting of about 7 to 15 blossoms and its production of new leaves and new blossom clusters every 20 days after first reaching a stem height of about 7 cm.

1 Drawing Sheet

This invention relates to a new hybrid variety of *Euphorbia milii* cv. Stiloga. The plant was discovered by Alfred Stirnadel in West Germany, and is a seedling resulting from the fertilization of Euphorbia dv. Gabriela (U.S. Plant Pat. No. 4,761) with a mixture of pollen from Euphorbia cv. Gabriela and Euphorbia cv. Suleika (U.S. Plant Pat. No. 4,931). Suleika is a selection from the selfing of Gabriela. It is noted that fertilization of Gabriela with pollen of the variety Suleika alone was not successful.

The new variety cv. Stiloga may be distinguished from other presently available Euphorbia cultivars by the following combination of characteristics: its upright and bushy habit with a very abundant branching forming a compact-round plant; its early production on strong solid short stalks of from about 10 to 15 blossom clusters, each cluster consisting of about 7 to 15 blossoms; its production of new leaves and new blossom clusters approximately every 20 days after first reaching a stem height of about 7 cm; its leaves of up to 4 cm in width and 8 cm in length; and its irregular number (2–8) of thorns forming a comb on small nodes, the nodes occurring at intervals of 0.8 to 1 cm along about five stem ridges. Stiloga holds these distinguishing characteristics through succeeding propagations by vegetative propagation.

The new variety cv. Stiloga may be distinguished from Gabriela, (U.S. Plant Pat. No. 4,761) by the following combination of characteristics. Whereas Gabriela has a slightly bushy habit and produces blossom clusters of about 32 single blossoms approximately every 10 to 14 days after first reaching a stem height of 10 cm, Stiloga has a compact, round and bushy habit with abundant branching and produces blossom clusters of about 10–15 single blossoms approximately every 20 days after reaching a stem height of about 7 cm. Small nodes occur on each of five stem ridges of Stiloga at intervals of 0.8 to 1 cm whereas the nodes of Gabriela occur at 2 cm intervals. Leaves of Stiloga are of varying widths and lengths, but usually up to about 4 cm in width and 8 cm in length. Leaves of Gabriela are also of varying widths and lengths, but are usually up to about 5 cm in width and 15 cm in length.

The new variety cv. Stiloga may be distinguished from Suleika (U.S. Plant Pat. No. 4,931) by the following combination of characteristics. Stiloga blooms continuously, new leaves and blossom clusters being produced uninterruptedly every 20 days or so whereas Suleika does not bloom continuously. Whereas Suleika limits its growth vertically to a height of about 10 to 12 cm, Stiloga grows continuously. Whereas the leaves of Suleika are obovate in shape and usually 4–9 cm long, leaves of Stiloga are slightly emarginate to very slightly mucronate and are usually up to 8 cm long. Suleika pedicels are usually about 4–9 cm in length whereas Stiloga pedicels are usually 5–6 cm in length.

The accompanying drawing illustrates the plant in color and shows the flowering thereof from bud to full bloom. Throughout this specification, color names beginning with a small letter signify that the name of that color as used in common speech is aptly descriptive. Color names beginning with a capital letter designate values based upon the R.H.S. colour chart of The Royal Horticultural Society.

PLANT

The plant grows in an upright and bushy habit with very abundant ramification, i.e. the main shoot and base side-shoots form a compact, round plant. Upon reaching a stem height of about 7 cm, approximately 10 to 15 blossom clusters are produced at the main- and side-shoots under appropriate conditions. New blossom clusters and leaves are produced approximately every 20 days.

STEM

The stem is silvery-green, and when aged turns a grey-green, is slightly succulent in texture, about 0.8 to 1.2 cm in diameter with 4 to 5 ridges on which small nodes occur at about 0.8 to 1 cm intervals. Nodes bear an irregular number (2–8) of thorns, about 0.1 to 0.8 cm in length, to form a comb. Thus the stem is generally pentagonal in cross-section, studded with thorn clusters.

LEAVES

The alternately arranged leaves extend almost horizontally outward from the stem and branches and ramification from the leaf axis is possible. The leaves have a short stalk. The vertical distance from one leaf to the other is about 0.5 to 1 cm.

Leaves are slightly pulpy, dark green in color (Green 139A) on the upper side and light green (between Green 139C and Green 139D) on the underside. Leaves are of varying lengths and widths, usually up to about 4 cm in width and 8 cm in length, averaging from about 3 to 4 cm in width. Leaves are spatulate, with tips varying from very slightly emarginate (shallowly notched) to very slightly mucronate with an acuminate base. The leaves have a thick middle vein and a short stalk. Thorn clusters are located on nodes on both sides of the leaf axis. A white milky sap exudes from all plant parts when subjected to injury.

BLOSSOMS

Blossom clusters, consisting of from 7 to 15 single blossoms (each having two salmon-pink to luminous salmon-red bracts), are borne on one pedicel with multiple ramification. In contrast to Gabriela, plants of the variety Stiloga have fewer ramifications and consequently, fewer single blossoms. Usually, the upper side of the bracts are bluish carmine (Red-52A) and the underside of the bracts are carmine rose (Red-52D). Almost no discoloration is present. New blossom clusters arise from each new leaf axis on light green stalks up to 3 mm in thickness and up to about 3 to 8 cm in length but are usually 5 to 6 cm in length. The flower stalks are very strong and solid. Each blossom cluster is of layered configuration since as a rule two new blossoms develop from each individual blossom (biaxial ramification). The bracts of an individual blossom surround the flower organs and are rounded off, slightly superposed, with a central indentation and are slightly sinous on both sides; they achieve a width of up to 15 mm. In the appropriate environment the plant will bloom uninterruptedly. Depending on the temperature and light condition the sapling stage of the single blossom has a duration of 8 to 14 days from the closed flower bud to the opening of the bracts (false blossoms) and the subsequent appearance of the female ovary. The individual blossom is yellowish and dull; the three-part female ovary appears during the sapling stage, and after 2 to 4 days, the pollinatable ovary withdraws and the male blossom organs (stamens) appear. The male stamen grows up to 4 mm in height.

What is claimed is:

1. A hybrid plant of *Euphorbia milli* cv. Stiloga and the parts thereof, substantially as shown and described herein and particularly characterized by the following combination of characteristics: its upright and bushy habit with very abundant branching forming a compact-round plant; its early production on strong solid short stalks of from about 10 to 15 blossom clusters each cluster consisting of about 7 to 15 single blossoms; its production of new leaves and new blossom clusters approximately every 20 days after first reaching a stem height of about 7 cm; its leaves of up to 4 cm in width and 8 cm in length; and its irregular number (2–8) of thorns forming a comb on small nodes, the nodes occuring at intervals of 0.8 to 1 cm along about five stem ridges.

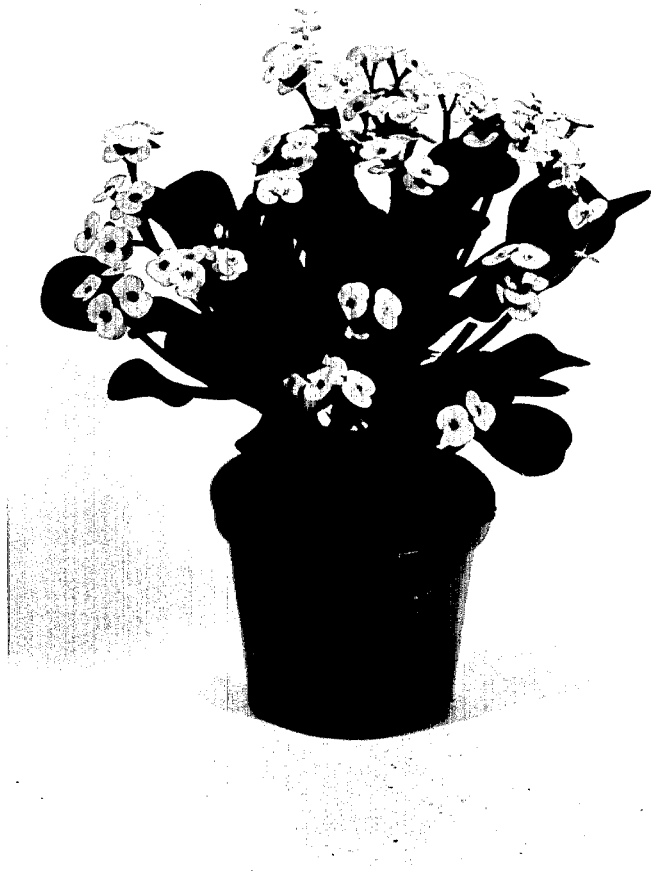

* * * * *